United States Patent [19]
Barnette et al.

[11] Patent Number: 5,626,848
[45] Date of Patent: May 6, 1997

[54] REDUCED-CLOUD-POINT CLARIFIED NEEM OIL AND METHODS OF PRODUCING

[75] Inventors: Deborah H. Barnette, Baltimore; James F. Walter, Ashton, both of Md.

[73] Assignee: Thermo Trilogy Corporation, Waltham, Mass.

[21] Appl. No.: 470,798

[22] Filed: Jun. 6, 1995

[51] Int. Cl.$^6$ .................................................. A01N 65/00
[52] U.S. Cl. .................. 424/195.1; 554/175; 514/453
[58] Field of Search .................. 424/195.1; 554/175; 514/453

[56] References Cited

U.S. PATENT DOCUMENTS

| | | | |
|---|---|---|---|
| 3,994,943 | 11/1976 | Gibble et al. | 260/420 |
| 4,276,227 | 6/1981 | Kirby et al. | 260/425 |
| 4,946,681 | 8/1990 | Walter | 424/195.1 |
| 5,001,146 | 3/1991 | Carter et al. | 514/453 |
| 5,124,349 | 6/1992 | Carter et al. | 514/453 |
| 5,281,618 | 1/1994 | Walter | 514/453 |
| 5,298,251 | 3/1994 | Locke et al. | 424/405 |
| 5,356,628 | 10/1994 | Locke et al. | 424/405 |
| 5,368,856 | 11/1994 | Locke et al. | 424/195.1 |
| 5,372,817 | 12/1994 | Locke et al. | 424/405 |
| 5,395,951 | 3/1995 | Nagasampagi et al. | 549/383 |
| 5,397,571 | 3/1995 | Roland et al. | 424/405 |
| 5,405,612 | 4/1995 | Locke et al. | 424/410 |
| 5,409,708 | 4/1995 | Locke et al. | 424/410 |
| 5,411,736 | 5/1995 | Locke et al. | 424/410 |

FOREIGN PATENT DOCUMENTS 1423636  2/1976  United Kingdom .

OTHER PUBLICATIONS

ASTM Designation D 2500–86, "Standard Test Method for Cloud Point of Petroleum Oils," pp. 268–270.

Lowery, D.T., et al., "Laboratory and Field Evaluation of Neem for the Control of Aphids (Homoptera: Aphidadae)," J.Econ. Entomol., 86:865–870 (1993).

Parmar, B.S., and S. Dutta, "Neem Oil as a Synergist for Insecticides," Neen Newsletter, 3:3–5 (1986).

Sharma, R.K., "Aphidicidal Action of Neem (Azadirachta indica A. Juss) on Mustard Aphid, Lipaphis erysimi (Kalt.)," Neem Newsletter, 3:1–2 (1986).

Primary Examiner—Margaret W. Glass
Attorney, Agent, or Firm—Quarles & Brady

[57] ABSTRACT

A clarified neem oil having a cloud point below 13° C. exhibits reduced phytotoxicity. Treatment of crude neem oil with a dilute aqueous basic solution or with an enzyme having lipid-degrading activity yields a clarified neem oil having acceptably low phytotoxicity. The methods are advantageous because they reduce or eliminate the waste stream of waxy by-product generated using existing methods for clarifying crude neem oil.

3 Claims, No Drawings

REDUCED-CLOUD-POINT CLARIFIED NEEM OIL AND METHODS OF PRODUCING

FIELD OF THE INVENTION

The present invention relates to the field of biocontrol agents isolated from neem trees and more particularly to a shelf-stable, low-phytotoxic neem oil having miticidal, fungicidal, and insecticidal properties.

BACKGROUND OF THE INVENTION

The neem tree, a tropical evergreen, has been used for centuries as a source of pesticides to which insects have not developed a resistance. Various neem seed extracts, particularly the ones containing the hydrophilic, tetranortriterpenoid azadirachtin, are known to influence the feeding behavior, metamorphosis (insect growth regulating [IGR] effect), fecundity, and fitness of numerous insect species belonging to various orders.

Neem oil, containing azadirachtin, may be mechanically pressed from neem seeds in the cold by using oil presses or may be extracted using alcohols or other solvents using a Soxhlet apparatus. Small amounts of neem oil can be obtained by kneading neem seed powder by hand after adding some water (Schmutterer & Helip 1988). Thus the term 'neem oil' has been used to describe a variety of materials containing a mixture of both hydrophilic and hydrophobic extractables. The variety of extraction methods and resultant variety in composition of neem oil has led to great confusion as to the true properties of "neem oil." Khan and Wassilew (1986) tested the effect of their "neem oil" (prepared by aqueous extraction of neem kernels) on 14 common fungi, including Trichophytonrubrum, *T. violaceus, T. concentrichus, T. mentagrophytes, Epidermophyton floccosum, Miersporum citaneum, Scrophulariopsis brevicaulis, Geotrichum candidum* and *Fusarium sp* and found that it did not inhibit fungal growth and, in fact, the neem oil itself actually contained several species of growing fungi. Yet an anonymous article (Anon. 1986) reported that "10% Neem oil diluted from its emulsifiable concentrate formulation" completely inhibited several species of fungi such as *Aspergillus niger, Fusarium moniliforme, Macrophomina phaseolina* and *Drechslera rostrata*. However, the specific details of this formulation were not provided.

Kahn et al. (1986) report that neem oil (source unidentified) showed no inhibitory affect on the growth of a variety of fungi. In fact, it is reported that the neem oil was contaminated with molds including *Aspergillus niger* and *Aspergillus flavus*. Similarly, Sharma et al. (1986) report that 3–5% neem seed oils (no method of preparation given) had no effect on the control of pod borer *Heliothis armigera* on chickpea, in Gujar et al. (1985) report that neem seed oil (no method of preparation given) had no effect on the desert locust *Schistocerca gregaria*.

Contrary to this, it has been reported that neem oil formulations prepared by expressing oil from the seeds or by extracting with aqueous solvents are effective insecticides and fungicides. It is reported that 10% neem oil (preparation unidentified) (Anon 1986) inhibited the growth of certain fungi in vitro. Dryer (1986) discloses that neem oil obtained by hand pressing in the cold was similar in the control of phytophagous arthropods to aqueous extracts; expeller-pressed oil was much less active.

Similarly, there are discrepancies in the literature as to the use of neem oil to control insects. Schmutterer and Hallpap (1986) showed that aqueous neem seed extracts are significantly superior to neem oil in repelling leaf mites (*Scrobipalpa ergasina*), leaf roller (*Phycita melogenu*) and leaf hopper (*Jacobiella faciaina*). Mansour et al. (1986) report that the pentane extract of neem seeds was much more effective at controlling the spider mite *Tetranychus cinnabarinus* than were ethanol or methanol extracts, but surprisingly, the pentane extract was less effective at controlling the mite, *Phytoseiulus persimilis* than were the ethanol or methanol extracts.

Yamasaki et al. showed that the tetranortriterpenoid salannin can be isolated from crude plant extracts, obtained from indian neem seeds which are known to be high in salannin content, using hexane. The biological activity of the salannin extract is reported to be feeding deterrency and growth inhibition when applied to chewing insects such as beetles and caterpillars.

Crude neem oil is not shelf-stable and can lose biocontrol activity. A solvent extraction method of U.S. Pat. No. 5,409,708, incorporated herein by reference, can be used to remove stability-reducing components from crude neem oil. This solvent-extraction method has the effect of reducing the cloud point of the crude neem oil, and increasing the shelf stability of the clarified product. However, the method requires a solvent-stripping step and an oil-fractionating step wherein certain waxes and fatty acids therein solidify and are filtered out. Moreover, the method significantly reduces the input neem oil volume and thereby creates a waste product stream that must be disposed of at significant expense to producers or consumers. According to the patent, when 35 pounds of crude neem oil were clarified by solvent extraction, 30 pounds of clarified oil and five pounds of neem wax were produced. Although both the clarified oil and the wax fractions are active, the clarified oil fraction is more effective for foliar applications, since the wax fraction exhibits higher phytotoxicity. Thus the wax fraction may find its most suitable use in formulations applied to dormant plants or non-plant material.

It would be desirable in the art, for both economic and other practical reasons, to produce a clarified neem oil having high shelf stability and low foliar phytotoxicity while minimizing the production of a neem wax byproduct.

SUMMARY OF THE INVENTION

The present invention is summarized in that reducing the cloud point of crude neem oil treating the crude oil with aqueous base or with lipase eliminates or virtually eliminates the waxy waste stream from the production process. The clarified neem oil produced in the claimed methods is a shelf-stable, low-phytotoxic insecticide, fungicide, and/or pesticide.

It is an object of the present invention to provide a method for producing shelf-stable, low phytotoxic clarified neem oil that avoids the limitations of prior methods, yet retains insecticidal, fungicidal, and/or pesticidal activity.

Other objects, features and advantages of the present invention will become apparent upon consideration of the following detailed description.

DETAILED DESCRIPTION OF THE INVENTION

Some active ingredients of the seeds and leaves of the tropical neem tree, *Azadirachtin indica*, particularly the tetranortriterpenoids azadirachtin and salannin, are known for their potent insecticidal activities. The present invention is directed to various insecticide and fungicide formulations prepared from non-polar hydrophobic solvent extracted neem oil which are substantially free of azadirachtin, yet possess the ability to repel insect pests from plant surfaces, kill insect pests at various life stages, in particular the egg and larval stage, and control fungal pathogens. The term "substantially free of azadirachtin" is used herein to indicate a neem oil having less than 1 weight percent of azadirachtin, preferably less than 0.2 weight percent of azadirachtin, most preferably less than 0.06 weight percent of azadirachtin.

As used herein, the term "insecticide" is intended to encompass insect repellents, larvacides, ovicides and the like. The term "insecticidally effective amount" or "fungicidally effective amount" means the dosage of active substance sufficient to exert the desired insecticidal or fungicidal activity. The term "crude neem oil" is used herein to designate a neem oil obtained from neem seeds by extraction or by mechanical expelling. The term "clarified neem oil" designates a neem oil having a cloud point of 12° C. or below. The terms "neem wax" or "neem wax fraction" are used herein interchangeably to designate a semi-solid neem wax fraction obtained from a crude neem oil. "Cloud-point" means the temperature at which a cloud of wax crystals first appears in a liquid when it is cooled. The cloud-point of a clarified neem oil prepared in accordance with the present invention is readily determined by ASTM D 2500-86 "Standard Test Method for Cloud-Point of Petroleum Oils." Reduction in cloud-point correlates generally with reduced amount of wax or lipid in an oil.

Neem seeds consist of two parts, a shell that does not contain oil or insecticidal activity and the kernel which contains oil and azadirachtin. Neem seeds can be quite variable in size, shape and composition. Seeds from around the world can be small and round like a pea or large and long like a bean. Also, the composition of seeds collected from throughout the world varies considerably, as is shown in Table A. In particular, we have found that oil derived from neem trees with high azadirachtin concentration is both insecticidal and fungicidal.

TABLE A

| Seeds Source | % Kernel in Seed | % Volatile | Content Oil % | AZAD mg/gsk* |
|---|---|---|---|---|
| Senegal (Pout) | 54 | 7 | 22 | 6.6 |
| India (Punjab) | 55 | 5.8 | 30 | 1.6 |
| Togo (Atkpame) | 57 | 7.3 | 27 | 4.5 |
| Haiti (Arcahie) | 51 | 12.0 | 19 | 2.7 |
| Ghana (Bawk) | 57 | 6.4 | 14 | 3.9 |

*gsk = gram seed kernel

The insecticide and fungicide formulations of this invention are prepared from crude neem oil which has been obtained from neem seeds. There are two principal methods for removing crude neem oil from neem seeds: expulsion, where the oil is pressed from the seeds, and extraction where the oil is removed from the seeds by solubilization in a solvent. Inherently, materials made by these methods have very different properties. Oil expelled from the seed will also contain water expelled from the seed by the same process. This aqueous material will carry along with it liminoids, such as azadirachtin, which themselves have insecticidal activity. The methods of the present invention can be practiced on either mechanically expelled crude neem oil or on crude neem oil produced by solvent extraction. Although either method can be used, solvent-extraction is preferred because it yields crude neem oil having less water and higher activity against insects.

Hydrophobic-solvent extracted crude neem oil, and a method for making same, are disclosed in U.S. Pat. No. 5,356,628, which is incorporated herein by reference. Briefly, ground neem seeds are about 5 mesh extracted with a non-polar hydrophobic solvent to remove crude neem oil. It is preferred to use a significant excess of solvent ($\geq 3:1$, w:w) to obtain good yields. The solvent must be suitably hydrophobic to prevent excess water from contaminating the product. Water in the extract will cause azadirachtin to be extracted from the seeds and result in hydrolysis of the extract. Suitable non-polar, hydrophobic solvents for use in extracting the crude neem oil from the ground neem seeds will include those solvents having high neem oil solubility and substantially no azadirachtin or water solubility. The preferred non-polar solvents include, but are not limited to, aliphatic hydrocarbons and halogenated aliphatic hydrocarbons such as pentane, hexane, heptane, octane, nonane, decane, isooctane, chloropentane, chlorohexane, and the like, and their isomers; petroleum distillates, petroleum ether, and the like; aromatics and substituted aromatics such as benzene, toluene, chlorobenzene, benzaldehyde, xylenes, and the like; and mixtures thereof. Various other non-polar solvents having the above characteristics are well known to those skilled in the art, and the choice of a particular solvent is not per se critical to the invention, provided that azadirachtin is substantially insoluble therein and neem oil has a high degree of solubility therein.

After extraction, substantially all of the solvent is removed from the extract by low temperature evaporation, preferably by vacuum evaporation, to yield the crude neem oil product. Crude neem oil can have up to 40% by weight of waxy contaminants before treatment in the methods of the present invention. The cloud point of crude neem oil is typically about 15° C.

The cloud-point of the crude neem oil can be reduced using aqueous base to precipitate out certain waxy contaminants or by adding lipase which reduces the waxy contaminants enzymatically.

In a first method for reducing the cloud-point of the crude neem oil, the crude neem oil is treated according to the dewaxing method of Levine (U.S. Pat. No. 4,035,402, incorporated herein by reference). The crude neem oil is cooled to a temperature at or below 6° F. (15° C.). An acceptable cloud point is 13° C., although 12° C. or 10° C. are more preferred. A cloud point below 10° C. is most preferred. Cooling the neem oil to 10° C. is suitable. A dilute basic aqueous solution is added to 10–30% by weight. The dilute basic solution can contain between 1 and 5% NaOH, or the stoichiometric equivalent of other alkali. The mixture is then agitated gently for about 30–60 minutes until precipitation of waxy solids (soap) is substantially complete. The amount of solid that precipitates is small—on the order of 100 grams per kilogram of crude neem oil. Precipitation is substantially complete when no additional precipitate forms. The desired agitation time is readily calculable by performing a standard time course experiment. When the precipitation is substantially complete, the precipitated solids are removed. The solids can be removed by any suitable method for separating waxy solid from liquid phase, but preferably are removed by centrifugation. Filtration of precipitated materials obtained by treatment with base has proven less useful in reducing cloud point and extending shelf life of the clarified product. Centrifugation is also preferred because residual aqueous material separates from the clarified oil.

In a second method, the crude neem oil obtained as described above, is treated with a lipid-degrading enzyme such as α-lipase to enzymatically reduce or eliminate the undesired waxy components. α-Lipase is commercially available in purified form from a number of commercial sources. Lipolase, available from Novo Nordisk, has been shown to be suitable. In the lipase method, the crude neem oil is brought to a temperature at which the enzyme retains lipid-degrading activity. This temperature is preferably in the range of 20° to 40° C. and is most preferably 30° C. Lipase is added along with water and the crude neem oil is agitated during the reaction time of about 30 minutes, or until a suitable percentage of the lipid material is degraded. It is preferred that greater than about 50% of the lipid material be degraded, and more preferred that greater than about 75% be degraded. It is most preferred that substantially all of the lipid material be degraded. The lipase enzyme is deactivated by heating the treated crude neem oil to a suitably high temperature (e.g. 95° C.) for a time sufficient to eliminate the activity (e.g., 20 minutes). Solid materials are removed from the crude oil (e.g., by filtration using 340 Whatman filter paper or other filtration equipment, or by centrifugation). About 98% recovery is achieved. The recovered clarified neem oil has a reduced cloud point and is shown below to have reduced phytotoxicity relative to crude neem oil.

Foliar phytotoxicity can be measured on a rating scale of 1.0–4.0, wherein 1.0 represents no effect on plants and 4.0 represents a severe effect, as is set forth below. The phytotoxicity of a material means the phytotoxicity caused by the material when applied to a plant. A rating of 2.8 or higher is unacceptably high, while a rating of 2.3 or lower is acceptably low. The phytotoxicity of neem oil prepared by either method is comparable to that of solvent-clarified neem oil, but significantly less byproduct is generated when the clarified oil is produced by the methods disclosed herein.

In the compositions and formulations of the invention, the clarified neem oil may be used alone or may be mixed with conventional inert agronomically acceptable (i.e. plant compatible and/or insecticidally inert) or physiologically-compatible (depending upon the intended use of the insecticide) adjuvants such as surfactants, stabilizers, antifoam agents and antidrift agents may also be added. Examples of compositions and formulations according to the invention include aqueous suspensions and dispersions, oily dispersions, pastes, emulsifiable concentrates, flowables, invert emulsions, and aerosol compositions.

The compositions and formulations are prepared in a known manner to one skilled in the art, for example by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents.

Adhesives such as carboxymethylcellulose and natural and synthetic polymers in the form of powders, granules or latices, such as gum arabic, polyvinyl alcohol, polyvinyl cellulose, and polyvinyl acetate, can be used in the formulations to improve the adherence of this insecticide.

The neem oil of the present invention may be employed alone and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists, etc., if desired, or in the form of particular dosage preparations for specific applications made therefrom such as solutions, emulsions, suspensions, powders, pastes, and granules which are thus ready for use.

In general, insecticidal and fungicidal formulations in accordance with this invention can be prepared by diluting the clarified neem oil with about 5 to 50%, preferably 5 to 20% and most preferably 7 to 15%, by volume, emulsifying surfactant and may optionally contain 0–1% PABA or other UV screening material. Suitable emulsifying surfactants include sorbitan esters, ethoxylated and propoxylated mono- and diglycerides, acetylated mono- or diglycerides, lactylated mono- or diglycerides, citric acid esters or mono- or diglycerides, sugar esters, polysorbates, poly-glycerol esters, and the like, and mixtures thereof. The preferred emulsifying surfactants are the polyoxyethylene derivatives of fatty acid partial esters of sorbitol anhydrides which are sold under the name Tween 20, Tween 40, Tween 60 and Tween 80. Prior to final application, these insecticidal and fungicidal formulations are typically diluted with water.

For foliar application it has been observed that rates of 0.1 to 10%, preferably 0.25 to 3%, clarified neem oil diluted in water are effective for control of insect pests and fungal diseases without unacceptable plant damage. Neem oil may also be used at various dilutions to control various pest and disease problems on turf, horticultural and agricultural crops as well as stored fruits and vegetables. The neem oil formulations have been shown to be effective at controlling such insects as Colorado Potato Beetle, Diamond-backed Moth, Whitefly, Mealy bug, Aphids, Hornworm, Lacebug, fleas, mosquitoes and flies and the like. They are also effective at controlling fungi such as mildews, rusts, dollar spot, brown patch, black spots, botrytis, and the like. Furthermore, the clarified neem oil can be used to control parasitic pests on mammals such as mites, lice, ticks, and scabies. The clarified neem oil can also treat symptoms such as eczema and dermatitis.

Therefore, the methods find significant practical and economic utility when applied to the production of clarified neem oil for formulation as an insecticide, pesticide or fungicide.

EXAMPLES

Example 1—302.5 grams of crude neem oil having a cloud point ~15° C. was chilled to 40° F. A chilled aqueous solution of 1.9 grams sodium bicarbonate and 127.7 grams water was added to the crude oil. This mixture was gently agitated for 60 minutes at 40° F. The mixture was then centrifuged at 10,000 RPM and 40° F. for 10 minutes. 250.66 grams of treated oil was recovered with a cloud point of 8° C. The treated oil was formulated for use as a pesticide and had no significant adverse effects on the plants.

Example 2—150 grams of crude neem oil having a cloud point of ~15° C. was chilled to 10° C. A solution of 20 grams of water and 0.75 grams of sodium bicarbonate was also chilled to 10° C. and then added to the chilled crude oil. The mixture was gently agitated at 10° C. for 30 minutes. The clarified oil was separated from the water and wax by centrifugation at 10° C. and 10,000 RPM for 40 minutes. The clarified oil was then filtered through 40 Whatman filter paper. 132.3 grams of treated oil was recovered having a cloud point of 11° C. This oil was formulated into a pesticide and had no significant adverse effects on the plants.

Example 3—100 grams of crude oil having a cloud point of ~15° C. was brought to 30° C. 0.4 ml of Lipolase (Novo Nordisk product) was added along with 0.4 ml of water. The solution was incubated at 30° C. with agitation for 30 minutes. The enzyme was then deactivated by heating the solution to 95° C. and holding it at temperature for 20 minutes. The oil was filtered using 340 Whatman filter paper. 98 grams of treated oil was recovered with a cloud point of 12° C. The treated oil was formulated into a pesticide and had no significant adverse effect on the plants.

Example 4—150 grams of crude neem oil having a cloud point of ~15° C. was chilled to 10° C. A solution of 20 grams of water and 0.25 grams of sodium bicarbonate was also chilled to 10° C. and then added to the chilled crude oil. The mixture was gently agitated at 10° C. for 30 minutes. The clarified oil was not separated from the water and wax by centrifugation. Instead, the oil mixture was just filtered through 40 Whatman filter paper. This oil was formulated into a pesticide and had no significant adverse effects on the plants. However, it was very cloudy and did not have the desired shelf-life characteristics.

Example 5—In a comparison of phytotoxicity of variously prepared neem oil on Impatiens, neem oil was prepared as in Examples 1 through 4 and formulated into a pesticide. Crude neem oil was also formulated into a pesticide. The positive controls were neem oil that had been de-waxed using a solvent clarification method and water.

After formulation, the oil products were diluted 1:100 with water and sprayed on flowering Impatiens, thoroughly wetting the plants. Damage is assessed the day following spraying. The results are averaged for three sprayings each spaced a week apart. The results are presented in the following Table:

| Test Sample | Rating |
| --- | --- |
| Oil as prepared using Example 1 | 2.3 A |
| Oil as prepared using Example 2 | 1.5 A |
| Oil as prepared using Example 3 | 2.0 A |
| Oil as prepared using Example 4 | 2.0 A |
| Solvent de-waxed oil | 2.1 A |
| Crude oil | 2.9 B |
| Water | 1.0 A |

A = Statistically equal results
Rating Scale
1.0 — No effect on plant
2.0 — Slight effect, minor bleaching on edges of flower or leaf
3.0 — Moderate effect, brown spots or edges of flower or leaf
4.0 — Severe effect, mostly brown flower or leaf All the clarified neem oil samples gave superior results in the phytotoxicity test over the crude oil. Damage as occurs with crude oil would be unacceptable in the commercial marketplace.

These examples are exemplary of, but not limiting on, the invention which is intended to encompass all such variations and modifications as come within the scope of the present invention.

We claim:

1. A method for preparing a neem oil having an acceptably low foliar phytotoxicity, the method comprising the steps of:

treating a crude neem oil preparation comprising lipid material with an amount of an enzyme having a lipid-degrading activity, at a temperature at which the enzyme retains the lipid-degrading activity to degrade a percentage of the lipid material until a clarified neem oil is formed;

inactivating the enzyme; and determining the foliar phytotoxicity of the enzyme-treated neem oil, wherein the foliar phytotoxicity of the clarified neem oil is lower than the foliar phytotoxicity of the crude neem oil.

2. A method as claimed in claim 1 wherein the enzyme-treated neem oil has a cloud point of 10° C. or lower.

3. A method as claimed in claim 1 wherein the foliar phytotoxicity of the enzyme-treated neem oil is 2.3 or lower.

* * * * *